United States Patent
Hayat et al.

(10) Patent No.: US 10,684,277 B2
(45) Date of Patent: Jun. 16, 2020

(54) COLORIMETRIC FILTER PAPER ASSAY FOR RAPID MONITORING OF CHOLESTEROL LEVEL

(71) Applicant: COMSATS University Islamabad, Islamabad (PK)

(72) Inventors: Akhtar Hayat, Lahore (PK); Muhammad Azhar Hayat Nawaz, Lahore (PK)

(73) Assignee: COMSATS Institute of Information Technology, Islamabad (PK)

( * ) Notice: Subject to any disclaimer, the term of this patent is extended or adjusted under 35 U.S.C. 154(b) by 268 days.

(21) Appl. No.: 15/991,572

(22) Filed: May 29, 2018

(65) Prior Publication Data
US 2019/0025294 A1    Jan. 24, 2019

(30) Foreign Application Priority Data
Jul. 24, 2017 (PK) .................... 408/2017

(51) Int. Cl.
| | | |
|---|---|---|
| *C12Q 1/60* | (2006.01) | |
| *G01N 33/92* | (2006.01) | |
| *G01J 3/00* | (2006.01) | |
| *G01N 33/52* | (2006.01) | |

(52) U.S. Cl.
CPC ............ *G01N 33/523* (2013.01); *C12Q 1/60* (2013.01); *G01N 33/92* (2013.01); *G01N 2400/18* (2013.01); *G01N 2800/044* (2013.01)

(58) Field of Classification Search
CPC .. G01N 33/523; G01N 33/92; G01N 2400/18; G01N 2800/044; C12Q 1/60
See application file for complete search history.

(56) References Cited

U.S. PATENT DOCUMENTS

| | | | | |
|---|---|---|---|---|
| 2002/0045272 | A1* | 4/2002 | McDevitt | ............. B01L 3/0289 436/518 |
| 2014/0170688 | A1* | 6/2014 | Matje | ...................... C12Q 1/26 435/11 |

OTHER PUBLICATIONS

Cesar A. Lopez et al., "Molecular Mechanism of Cyclodextrin Mediated Cholesterol Extraction", PLOS Computational Biology, www.ploscompbiol.org., Mar. 2011, vol. 7, Issue 3, pp. 1-11.
Kazuo Taguchi, "Transient Binding Mode of Phenolphthalein-B-Cyclodextrin Complex: An Example of Induced Geometrical Distortion", Journal American Chemical Society, 1986, vol. 108, pp. 2705-2709.

* cited by examiner

*Primary Examiner* — Jennifer Wecker
*Assistant Examiner* — Michael Paul Shimek
(74) *Attorney, Agent, or Firm* — H.C. Park & Associates, PLC (57) ABSTRACT

A method for colorimetric detection of cholesterol in a sample is disclosed. The method includes adding beta-cyclodextrin and cholesterol to a phenolphthalein indicator solution in the presence of a phosphate buffer solution to create a solution medium and quantifying the cholesterol as a function of a complexed beta-cyclodextrin in the solution medium.

19 Claims, 8 Drawing Sheets
(6 of 8 Drawing Sheet(s) Filed in Color)

COLORIMETRIC FILTER PAPER ASSAY FOR RAPID MONITORING OF CHOLESTEROL LEVEL

CROSS-REFERENCE TO RELATED APPLICATION

This application claims priority from and the benefit of Pakistan Patent Application No. 408/2017, filed on Jul. 24, 2017, which is hereby incorporated by reference for all purposes as if fully set forth herein.

BACKGROUND

Field

Exemplary embodiments of the invention relate generally to using non-enzymatic filter paper based assay for monitoring a cholesterol level in a human serum.

Discussion of the Background

Biomarkers are biomolecules that can be correlated to a normal or pathogenic process in a biological medium, such as exposure level to environmental factors, genetic susceptibility, and response to the therapy induced changes. In this context, cholesterol is considered as one of the most important and reliable biomarker for cardiovascular disease and high blood pressure. Cholesterol constitutes an important component of cell membranes and is considered as the main precursor for synthesis of different type of biomolecules including bile acids, steroid hormones, and vitamin D. The normal level of total cholesterol in human serum is between 1.3-2.6 mg mL$^{-1}$, while 30% of this is present as sterol and remaining 70% is esterified with fatty acids. Higher concentration of cholesterol in blood serum forms plaques in the arteries of blood vessels, resulting in the prevention of blood circulation. The diseases associated with abnormal levels of cholesterol include hypertension, coronary heart disease, arteriosclerosis, brain thrombosis, lipid metabolism of dysfunction, and myocardial infraction. Thus, the development of rapid, cost effective methodologies to monitor cholesterol level in human serum is highly desirable in the field of clinical diagnosis.

The previous literature has focused on the design of various cholesterol detection methodologies. The colorimetric spectrophotometric detection and high performance liquid chromatography methods are very common, but are limited in their applications due to the expensive equipment and time-consuming. Alternatively, electrochemical enzymatic biosensors based on the enzymatic reaction of cholesterol with cholesterol oxidase or mediated bioelectrocatalytic oxidation of cholesterol were evolved to overcome the above mentioned problems associated with the classical methods. These enzymatic methods offer some good advantages such as high selectivity, enhanced sensitivity and feasibility for real time applications. However, their intrinsic nature is highly dependent on the factors such temperature, solution pH, humidity, and toxic chemicals, which results in the instability of the enzymatic activity. The enzymatic biosensors also undergo problem of denaturation during their immobilization on the transducer platform. These issues widely hindered the applications of existing methodologies for cholesterol monitoring. In spite of significant progress, available methods are still expensive, require sample collection and transport at a centralized lab, skilled personnel and specialized equipment for analysis and signal quantification. Only a limited number of samples can be tested and predictive or early warning information is missing. This is a significant impediment to provide timely counter-measures, especially in remote locations and in countries with limited resources. Easy-to-use methods that can be deployed remotely to site locations coupled with effective communication components are highly needed for clinical diagnosis of cholesterol level.

The above information disclosed in this Background section is only for understanding of the background of the inventive concepts, and, therefore, it may contain information that does not constitute prior art.

SUMMARY

Systems and methods according to exemplary embodiments of the invention are capable of inexpensively using non-enzymatic filter paper based assay for monitoring a cholesterol level in a human serum.

According to one or more embodiments of the invention, a method for colorimetric detection of cholesterol in a sample, the method includes adding beta-cyclodextrin and cholesterol to the phenolphthalein indicator solution with a phosphate buffer solution to create a solution medium, and quantifying the cholesterol as a function of a complexed beta-cyclodextrin in the phenolphthalein indicator solution.

The method may further include comparing the efficiency of the beta-cyclodextrin to a quenched phenolphthalein in the phosphate buffer solution at different pHs.

The change in a pH of the phosphate buffer solution may be associated with a color intensity of phenolphthalein.

The method may further include comparing the beta-cyclodextrin complexation with the cholesterol at different pHs in the phosphate buffer solution.

The method may further include recording the cholesterol complexation with the beta-cyclodextrin under varying concentrations of the cholesterol.

The method may further include detecting different concentrations of the cholesterol by monitoring recovery of the phenolphthalein color using ultraviolet/visible spectrophotometer, and determining an amount of total cholesterol present in a sample based on the detection. The recovery of phenolphthalein color may be based on competitive binding between the cholesterol and phenolphthalein for the beta-cyclodextrin.

According to one or more exemplary embodiments of the invention, a method for colorimetric detection of cholesterol in a human serum sample using a filter paper based transducer platform, the method including the steps of providing sonication time and concentration of the beta-cyclodextrin for the modification of a filter paper with the beta-cyclodextrin, quantifying the cholesterol based on recovery of the beta-cyclodextrin quenched phenolphthalein color on the filter paper based transducer platform, checking a response of cholesterol interfering compounds for a filter paper based assay, and detecting the cholesterol in human serum samples.

Color recovery of phenolphthalein in the presence of cholesterol may be achieved on beta-cyclodextrin modified filter paper transducers subject to different sonication time intervals during modification, indicating sonication time dependency on color recovery.

The filter paper may be modified with a range of different concentrations of the beta-cyclodextrin.

The quantitative analysis for monitoring cholesterol may be performed and a linear response in the form of increasing phenolphthalein color recovery may result with an increase in cholesterol concentration.

The method may further include the step of comparing the phenolphthalein color recovery for a given cholesterol concentration at different time intervals.

The specificity and selectivity of developed paper based sensor for the cholesterol may be established in the presence of an interfering compound. The interfering compound may be selected from the group consisting of glucose, ascorbic acid, and uric acid.

The stability of a filter paper based sensor may be evaluated for extended intervals of time.

According to yet another exemplary embodiment of the invention, a system for the colorimetric determination of cholesterol in a sample, the system includes a sample, a beta-cyclodextrin modified filter paper, a phenolphthalein indicator solution in phosphate buffer solution, a smart phone, and software to process images.

The images may be taken with the smart phone or are scanned with a color photo scanner. The images may be saved as Joint Photographic Expert Group (JPEG) images.

The saved JPEG images may be imported into image processing software and examined with different software tools.

The saved JPEG images may be disintegrated into red, green, and blue (RGB) components.

The detection of a lowest concentration of the cholesterol may be achieved with greatest sensitivity by permitting a green (G) color channel for analysis.

According to yet another exemplary embodiment of the invention, a method, including adding a phenolphthalein indicator solution in a phosphate buffer solution to a modified filter paper containing beta-cyclodextrin, adding a sample containing cholesterol to the modified filter paper to create a finalized filter paper, taking an image of the finalized filter paper, and determining a total amount of cholesterol in the sample by comparing the image of the finalized filter paper to control images.

Additional features of the inventive concepts will be set forth in the description which follows, and in part will be apparent from the description, or may be learned by practice of the inventive concepts.

It is to be understood that both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, and/or aspects, etc. (hereinafter individually or collectively referred to as "elements"), of the various embodiments may be otherwise combined, separated, interchanged, and/or rearranged without departing from the inventive concepts.

When an exemplary embodiment may be implemented differently, a specific process order may be performed differently from the described order. For example, two consecutively described processes may be performed substantially at the same time or performed in an order opposite to the described order. Also, like reference numerals denote like elements.

For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

This invention addresses a significant technology gap by developing inexpensive site portable-ready to use non enzymatic filter paper based assay for the monitoring of cholesterol level in the human serum. The developed method integrated the beta-cyclodextrin as a host on the filter paper based transducer platform to competitively recognize cholesterol and phenolphthalein as binding guests. Recently, filter paper has received wider interest as a potential transduction platform in the field of sensors/biosensors due to its large surface area and low cost. Paper based sensing platforms have emerged as potential and attractive alternative devices for many analytical applications. The simplicity of fabrication, biocompatibility, portability, and disposability in combination with the small volume of reagent/sample solutions make them highly suitable to design portable, easy to use and cost effective analytical devices.

Beta-cyclodextrin is a cyclic polysaccharide comprised of seven glucose molecules. Beta-cyclodextrin has been employed for selective extraction of cholesterol from the bioenvironment. Its hydrophilic outer surface provides the water solubility, while hydrophobic inner cavity is used for specific recognition of guest molecules. The host-guest interaction of beta-cyclodextrin has been used for the extraction of cholesterol from food, cell membrane, blood serum, and cultured cells (Lopez C A, de Vries A H, Marrink S J., *Molecular Mechanism of Cyclodextrin Mediated Cholesterol Extraction*, PLoS COMPUTATIONAL BIOLOGY 2011; 7:e1002020). This literature suggests that beta-cyclodextrin can be employed as a synthetic alternative to natural enzyme/antibody for selective binding/recognition of the cholesterol. However, this interaction does not produce any detectable signal or optical change to make this host-guest interaction feasible for qualitative and quantitative monitoring of cholesterol.

Figure 1A:
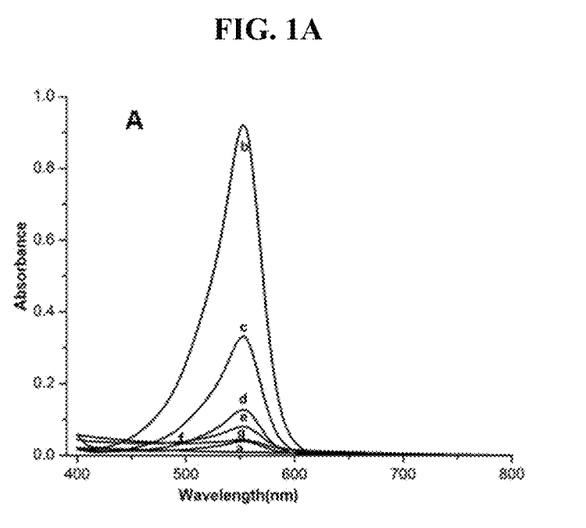
FIG. 1A is an absorption spectrum of phenolphthalein in the presence of varying concentrations of beta-cyclodextrin.
Figure 1B:
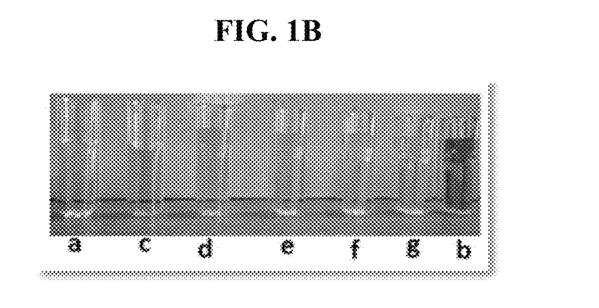
FIG. 1B is a visual image of quenching in the color/optical properties of phenolphthalein upon incubation with various concentrations of beta-cyclodextrin.
Figure 1C:
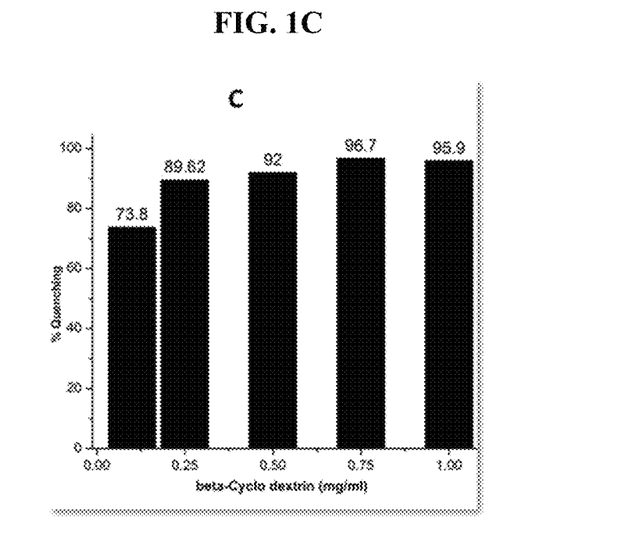
FIG. 1C shows the calibration plot of percentage quenching against various concentrations of beta-cyclodextrin.

Phenolphthalein interaction with beta-cyclodextrin can be integrated into the system to get the detectable optical signals. Phenolphthalein can be transferred from its pink color into colorless lactonoid dianion with in the cavity of beta-cyclodextrin (Taguchi K., *Transient Binding Mode of Phenolphthalein-P-Cyclodextrin Complex: An Example of Induced Geometrical Distortion*, JOURNAL OF THE AMERICAN CHEMICAL SOCIETY, 1986; 108:2705-9). Based on these scientific approaches, a portable and cost effective filter paper based methodology was developed for the quantitative monitoring of cholesterol in the human serum samples. Cholesterol and phenolphthalein were allowed to competitively bind with the guest beta-cyclodextrin, and a lower quenching percentage was observed with increasing concentration of cholesterol, which was subsequently used to draw a calibration curve In order to demonstrate the principle of methodology, ultraviolet-visible (UV/Vis) spectrophotometer assays were initially performed in a solution medium. FIG. 1A shows the UV/Vis spectrum of phenolphthalein in the presence of varying concentrations of beta-cyclodextrin, while FIG. 1B shows the visual images of quenching in the color/optical properties of phenolphthalein upon incubation with various concentrations of beta-cyclodextrin. As shown in these two figures, (a) corresponds to 0.75 mg/mL of beta-cyclodextrin, (b) corresponds to 35 µM of Phenolphthalein, (c) corresponds to 35 µM of phenolphthalein with a concentration of 0.1 mg/mL of beta-cyclodextrin in a phosphate buffer at a pH of 7, (d) corresponds to 35 µM of phenolphthalein with a concentration of 0.25 mg/mL of beta-cyclodextrin in a phosphate buffer at a pH of 7, (e) corresponds to 35 µM of phenolphthalein with a concentration of 0.5 mg/mL of beta-cyclodextrin in a phosphate buffer at a pH of 7, (f) corresponds to 35 µM of phenolphthalein with a concentration of 0.75 mg/mL of beta-cyclodextrin in a phosphate buffer at a pH of 7, (g) corresponds to 35 µM of phenolphthalein with a concentration of 1 mg/mL of beta-cyclodextrin in a phosphate buffer at a pH of 7. As can be seen from FIGS. 2A and 2B, quenching efficiency was increased with increasing concentrations of beta-cyclodextrin, demonstrating the capturing of phenolphthalein molecules in the cavity of beta-cyclodextrin. Further to optimize the concentration of beta-cyclodextrin, percentage quenching efficiency was calculated based on these experiments, FIG. 1C shows the calibration plot of percentage quenching against various concentrations of beta-cyclodextrin. A maximum percentage quenching of 96.7% was obtained at beta-cyclodextrin concentration of 0.75 mg/mL, which was employed for further experiments. Furthermore, it was observed that quenching/complexation phenomena is instantaneous and does not require any incubation time.

Figure 2A:
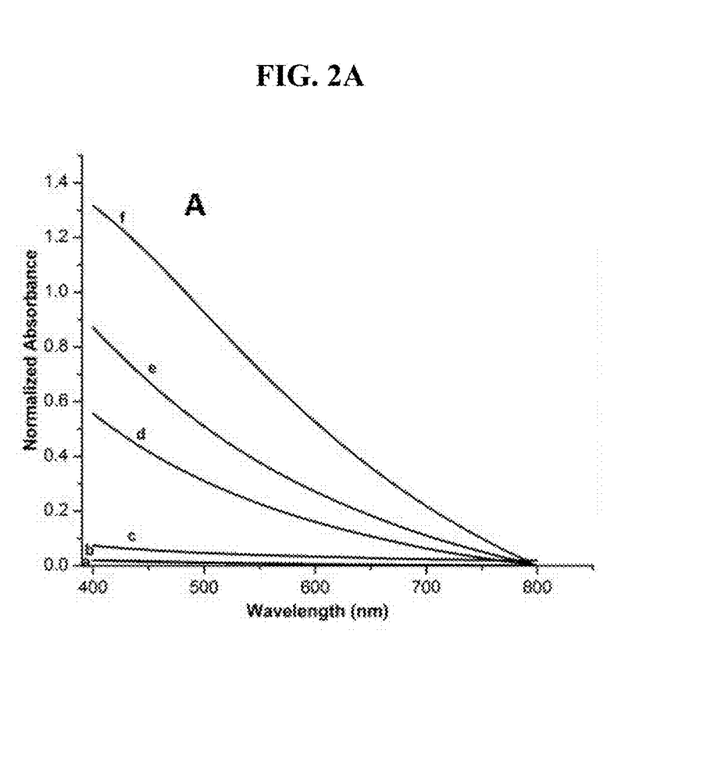
FIG. 2A is a UV/Vis spectrum of beta-cyclodextrin under varying concentrations of cholesterol.
Figure 2B:
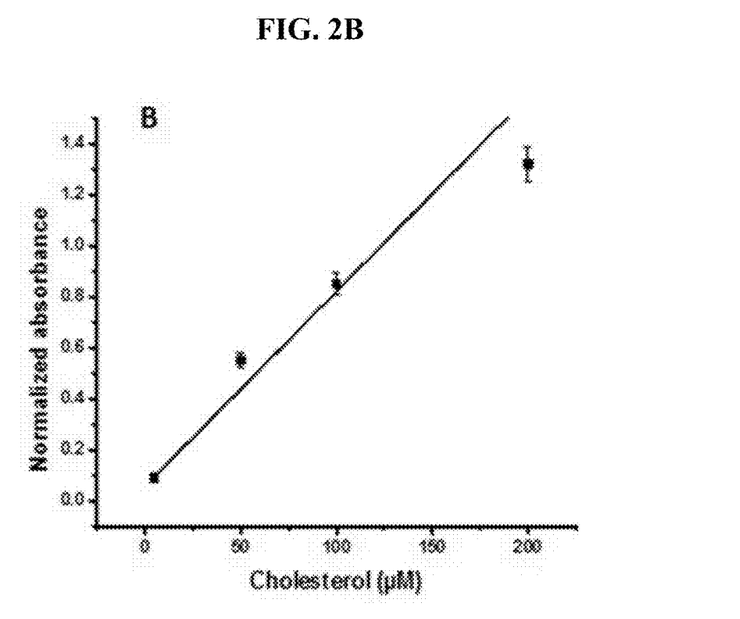
FIG. 2B shows a calibration curve in terms of normalized absorbance against various concentrations of cholesterol.

The next step was to demonstrate the host-guest interaction between beta-cyclodextrin and cholesterol. UV-Vis experiments were performed to have an insight on the coupling of two molecules. FIG. 2A shows the UV/Vis spectrum of beta-cyclodextrin under varying concentrations of cholesterol. In FIG. 2A, (a) correspond with 0.75 mg/mL beta-cyclodextrin, (b) corresponds with 100 µM cholesterol, (c) corresponds with 0.75 mg/mL beta-cyclodextrin with 5 µM of cholesterol in a phosphate buffer at a pH of 7, (d) corresponds with 0.75 mg/mL beta-cyclodextrin with 50 µM of cholesterol in a phosphate buffer at a pH of 7, (e) corresponds with 0.75 mg/mL beta-cyclodextrin with 100 µM of cholesterol in a phosphate buffer at a pH of 7, (f) corresponds with 0.75 mg/mL beta-cyclodextrin with 200 µM of cholesterol in a phosphate buffer at a pH of 7. An increase in the absorbance response was observed with increasing concentrations of cholesterol. For example, (f), having 200 µM of cholesterol, had the highest normalized absorbance. Control experiments with beta-cyclodextrin and cholesterol solutions were also carried out to elucidate the biding between two molecules. It is believed that a linear increase in absorbance with cholesterol concentration is indicative of the complexation between cholesterol and beta-cyclodextrin. FIG. 2B shows the corresponding calibration curve in term of normalized absorbance against various concentrations of cholesterol. Similarly, time dependence study revealed that complexation phenomena is instantaneous and does not need longer incubation time.

After successful demonstration of beta-cyclodextrin host-guest complexation with phenolphthalein and cholesterol, assay principle for the quantitative detection of cholesterol was performed in the solution. The addition of beta-cyclodextrin to phenolphthalein solution resulted in complete color disappearance of the solutions, indicating its quenching/capturing nature for the guest. However, addition of cholesterol induced a competitive binding between two guests for beta-cyclodextrin, and the quenching efficiency was decreased with a recovery of the phenolphthalein color.

Figure 3A:
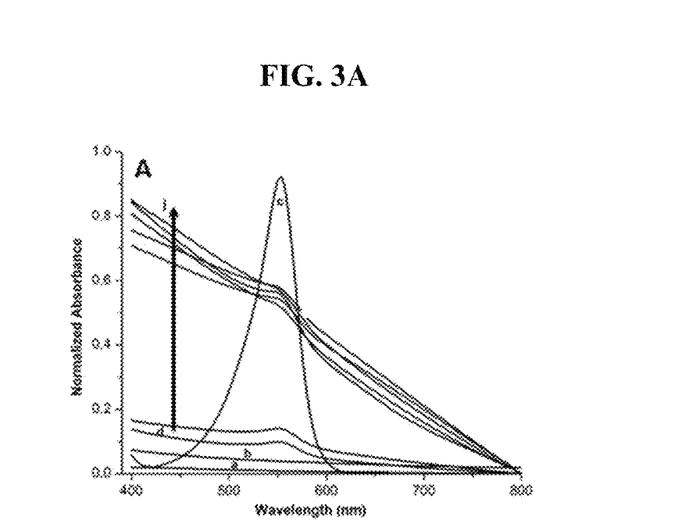
FIG. 3A shows UV/Vis spectra of recovered absorbance in the presence of various concentrations of cholesterol.
Figure 3B:
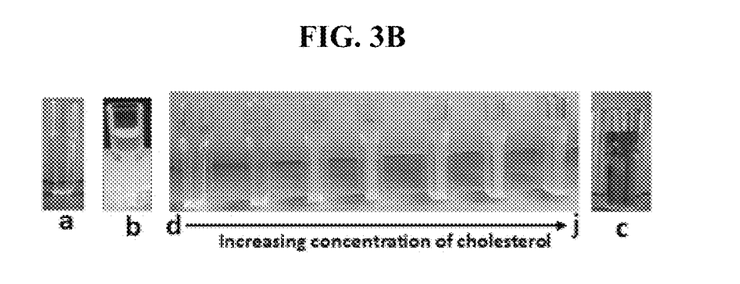
FIG. 3B are images of concentration recovery.
Figure 3C:
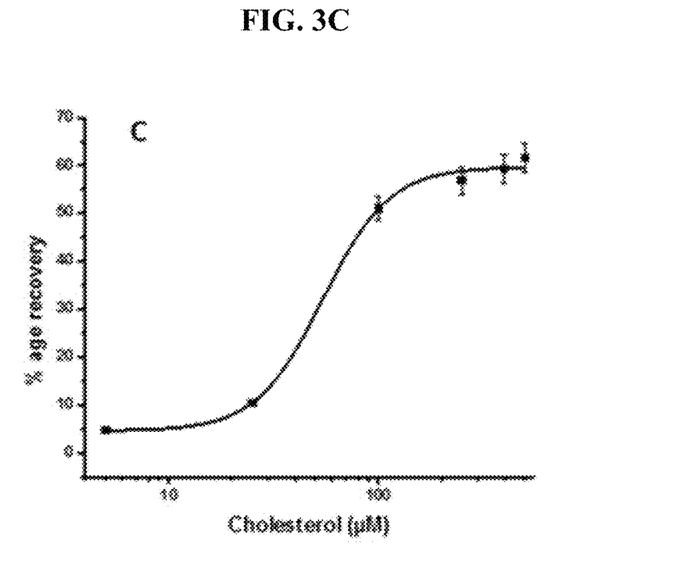
FIG. 3C shows a calibration curve in terms of percentage recovery against various concentrations of cholesterol.

FIG. 3A represents the UV/Vis spectra of recovered absorbance in the presence of various concentrations of cholesterol, while visual images of corresponding concentrations recovery in color are presented in the FIG. 3B. In FIGS. 3A and 3B, (a) corresponds with 0.75 mg/mL beta-cyclodextrin, (b) corresponds with 100 µM of cholesterol, (c) corresponds with 35 µM phenolphthalein, (d) corresponds with 35 µM of phenolphthalein and 0.75 mg/mL beta-cyclodextrin with 5 µM of cholesterol in a phosphate buffer at a pH of 7, (e) corresponds with 35 µM of phenolphthalein and 0.75 mg/mL beta-cyclodextrin with 25 µM of cholesterol in a phosphate buffer at a pH of 7, (f) corresponds with 35 µM of Phenolphthalein and 0.75 mg/mL beta-cyclodextrin with 100 µM of cholesterol in a phosphate buffer at a pH of 7, (g) corresponds with 35 µM of phenolphthalein and 0.75 mg/mL beta-cyclodextrin with 175 µM of cholesterol in a phosphate buffer at a pH of 7, (h) corresponds with 35 µM of phenolphthalein and 0.75 mg/mL beta-cyclodextrin with 250 µM of cholesterol in a phosphate buffer at a pH of 7, (i) corresponds with 35 µM of phenolphthalein and 0.75 mg/mL beta-cyclodextrin with 400 µM of cholesterol in a phosphate buffer at a pH of 7, and (j) corresponds with 35 µM of phenolphthalein and 0.75 mg/mL beta-cyclodextrin with 500 µM of cholesterol in a phosphate buffer at a pH of 7. FIG. 3C shows a calibration curve in terms of percentage recovery against various concentrations of cholesterol.

As can be seen from FIGS. 3A, 3B, and 3C, the color recovery was linearly related to the concentration of cholesterol. Based on the UV/Vis absorption spectra, percentage recovery in color was calculated and plotted against cholesterol concentrations. The assay response was linearly proportional to cholesterol concentration in the range of 20 µM to 125 µM, with a limit of detection of 10 µM. A standard deviation of 5% was observed with this colorimetric assay. After successful demonstration of the assay principle in an aqueous medium, the next step was to transfer this concept and methodology on the filter paper based transducer platform.

The initial tests were performed to investigate the behavior of cholesterol on the unmodified and modified filter papers.

Figure 4A:
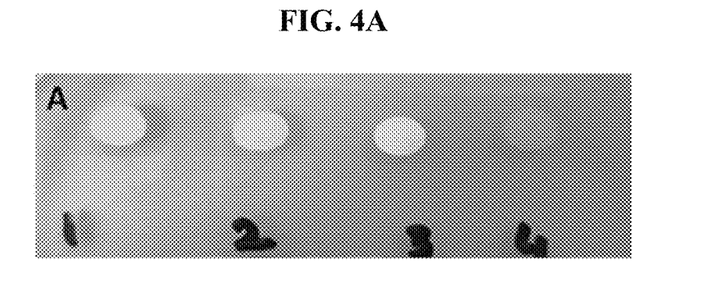
FIG. 4A is an image of unmodified filter paper, unmodified filter paper with cholesterol, beta-cyclodextrin modified filter paper, and modified filter paper with cholesterol.

FIG. 4A is an image of unmodified filter paper, unmodified filter paper with cholesterol, beta-cyclodextrin modified filter paper, and modified filter paper with cholesterol. In FIG. 4A, (1) corresponds with unmodified filter paper, (2) corresponds with unmodified filter paper with 125 µM cholesterol, (3) corresponds with modified filter paper with 0.1 mol/L beta-cyclodextrin, (4) corresponds with modified filter paper with 125 µM cholesterol. FIG. 4A shows that the presence of cholesterol on modified/unmodified filter paper does not induce any change in the optical properties of the filter paper. Similarly, beta-cyclodextrin modification also did not results any change in the surface optical properties of the paper. These experiments revealed the non-interfering optical characteristic of the used reagents on the filter paper based transducer platform.

Figure 4B:
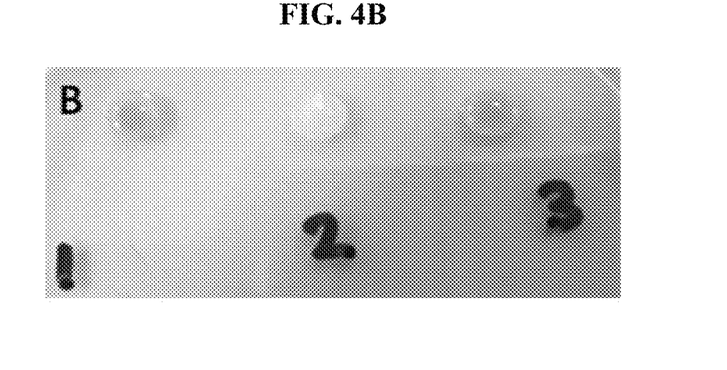
FIG. 4B is an image of unmodified filter paper with phenolphthalein, modified filter paper with beta-cyclodextrin and phenolphthalein, and modified filter paper with beta-cyclodextrin, phenolphthalein, and cholesterol.

FIG. 4B is an image of unmodified filter paper with phenolphthalein, modified filter paper with beta-cyclodextrin and phenolphthalein, and modified filter paper with beta-cyclodextrin, phenolphthalein, and cholesterol. In FIG. 4B, (1) corresponds with unmodified filter paper with 10 µL of 100 µM phenolphthalein, (2) corresponds with modified filter paper with 0.1 mol/L of beta-cyclodextrin and 10 µL of 100 µM phenolphthalein, and (3) corresponds with modified filter paper with 0.1 mol/L of beta-cyclodextrin and 10 µL of 100 µM phenolphthalein with 125 µM cholesterol. FIG. 4B demonstrate the assays principle. A very strong pink color of phenolphthalein was observed on the unmodified filter paper, while this color was completely quenched on the beta-cyclodextrin modified paper, indicating that beta-cyclodextrin has retained host-quest characteristics for phenolphthalein capturing. In the same context, incubation of cholesterol along with phenolphthalein hindered the quenching characteristics of beta-cyclodextrin towards phenolphthalein, and pink color was recovered. This phenomenon can be explained by the fact that the presence of cholesterol molecules on the modified filter has resulted in complexation with beta-cyclodextrin and hence reduced the number of beta-cyclodextrin available cavities to capture and further quench the color of phenolphthalein. Based on the above observed mechanism, it was possible to monitor cholesterol quantitatively, and design an easy to use, portable and decentralized filter paper based assay for clinical analysis of cholesterol. However, prior to performing quantitative analysis, it was very important to optimize certain experimental aspects for better analytical figure of merits of the assay. The first step to optimize was the sonication time in the modification of filter paper with beta-cyclodextrin.

Figure 4C:
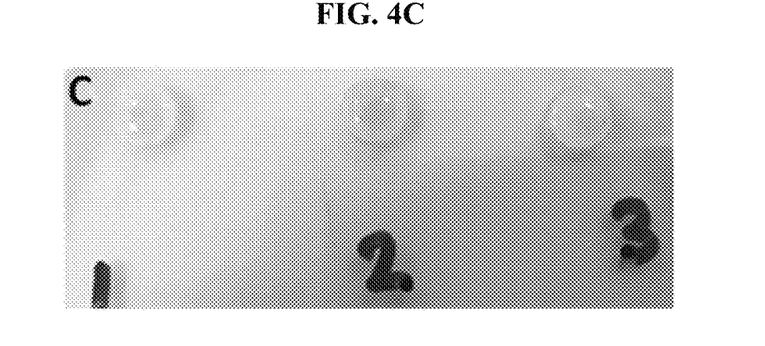
FIG. 4C is an image showing the effect of sonication time on the modification of filter paper with beta-cyclodextrin based on the percentage recovery of phenolphthalein color upon incubation with cholesterol.

FIG. 4C is an image showing the effect of sonication time on the modification of filter paper with beta-cyclodextrin based on the percentage recovery of phenolphthalein color upon incubation with cholesterol. Modified filter paper with sonication time ranging from 45 min and 80 min were fabricated and recovery in the optical properties of for each modified filter paper was observed in the presence of cholesterol. As shown in FIG. 4C, (1) corresponds with a sonication time of 45 minutes, (2) corresponds with a sonication time of 60 minutes, and (3) corresponds with a sonication time of 80 minutes. As can be seen from the FIG. 4C, better recovery in the response was observed when a beta-cyclodextrin filter paper with a sonication time of 60 min was applied. The further optimization experiments were performed with this type of filter paper under a sonication time of 60 min.

In the same context, next step was to optimize the concentration of beta-cyclodextrin for the modification of filter paper. Filter paper with higher concentrations of beta-cyclodextrin may give a better response in term of quenching efficiency but can result in decreased recovered response after cholesterol incubation.

Figure 5A:
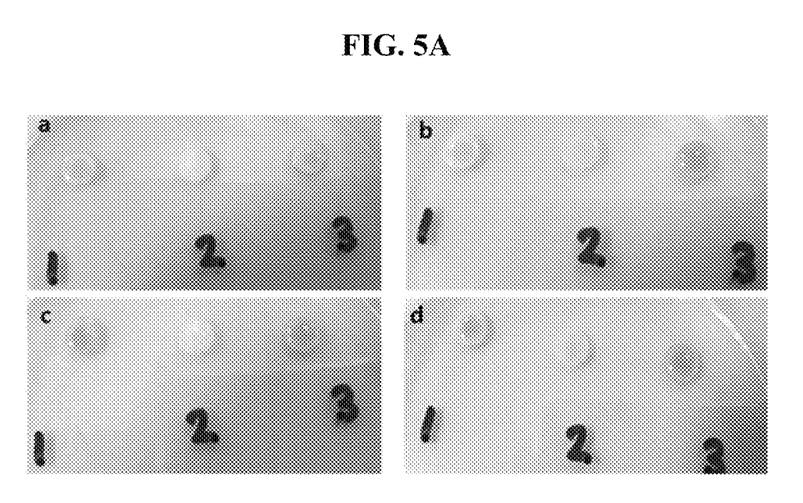
FIG. 5A are images showing the effect of beta-cyclodextrin concentration on modified filter paper based on the percent recovery of phenolphthalein color upon the incubation of cholesterol.
Figure 5B:
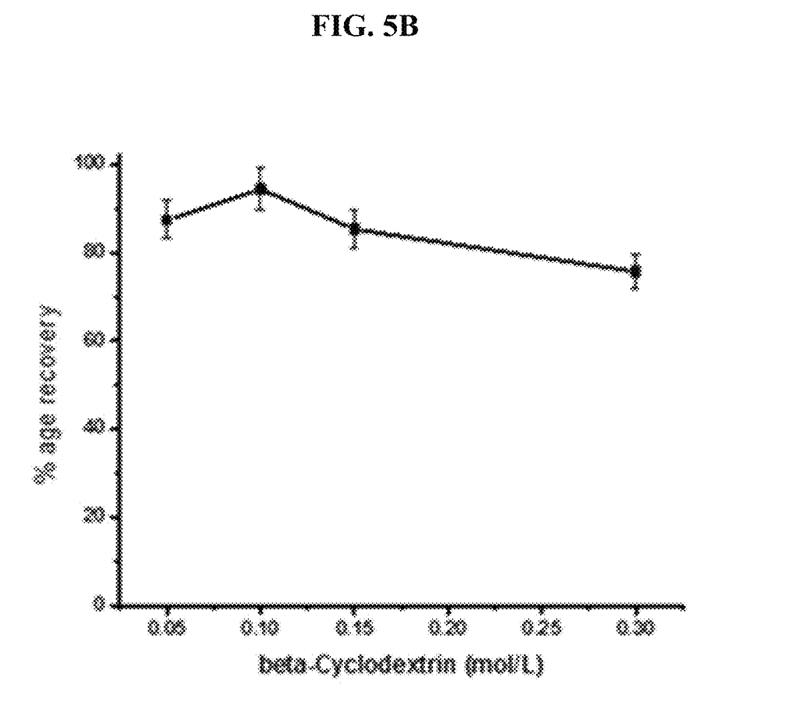
FIG. 5B shows the calibration plot of percentage recovery against various concentrations of beta-cyclodextrin.

FIG. 5A are images showing the effect of beta-cyclodextrin concentration on modified filter paper based on the percent recovery of phenolphthalein color upon the incubation of cholesterol. FIG. 5B shows the calibration plot of percentage recovery against various concentrations of beta-cyclodextrin. Filter paper with beta-cyclodextrin concentrations ranging from 0.05 mol/L to 0.3 mol/L were prepared and their recovery results in the presence of cholesterol were obtained to have an insight on the optimal concentration of beta-cyclodextrin. In FIG. 5A, (a) corresponds to a beta-cyclodextrin concentration of 0.3 mol/L, (b) corresponds to a beta-cyclodextrin concentration of 0.15 mol/L, (c) corresponds to a beta-cyclodextrin concentration of 0.1 mol/L, and (d) corresponds to a beta-cyclodextrin concentration of 0.05 mol/L. Also in FIG. 5A, (1) corresponds with unmodified filter paper with 10 µL of 100 µM phenolphthalein, (2) corresponds with modified filter paper with beta-cyclodextrin and 10 µL of 100 µM phenolphthalein, and (3) corresponds with modified filter paper with beta-cyclodextrin and 10 µM of 100 µM phenolphthalein upon incubation with 125 µM cholesterol. As can be observed from the visual figures in FIG. 5A as well as from the calibration plot of FIG. 5B, better recovery response was seen when filter paper was modified with a beta-cyclodextrin concentration of 0.1 mol/L.

Figure 6A:
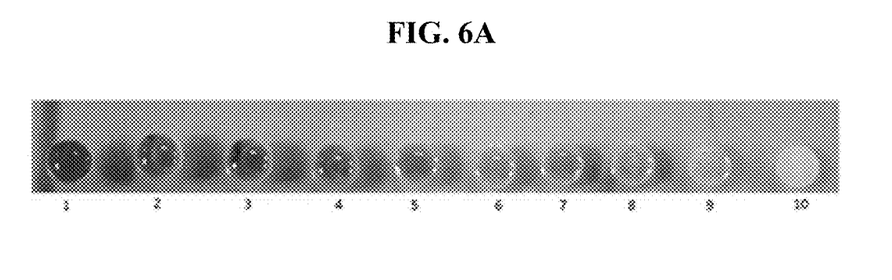
FIG. 6A is an image showing the visual images of the recovered response under varying concentrations of cholesterol.
Figure 6B:
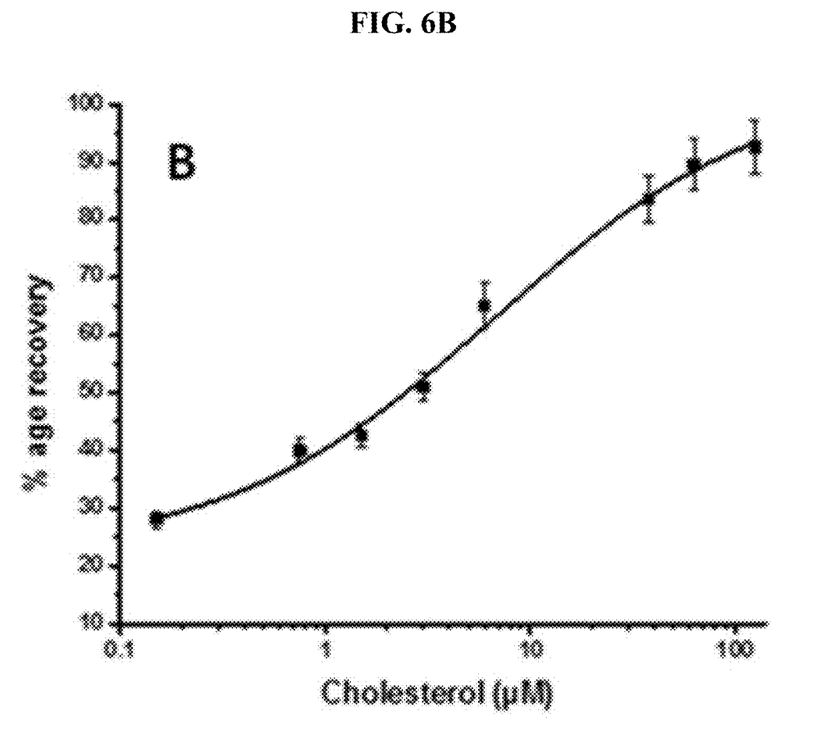
FIG. 6B shows a calibration curve in terms of percent recovery against various concentrations of cholesterol.

FIG. 6A is an image showing the visual images of the recovered response under varying concentrations of cholesterol. FIG. 6B shows a calibration curve in terms of percent recovery against various concentrations of cholesterol. After optimization of experimental conditions, quantitative analysis for the monitoring of cholesterol were performed on the filter paper based transducer platform. The obtained results for cholesterol detection with our designed assays are presented in FIGS. 6A and 6B. In FIG. 6A, (1) corresponds with unmodified filter paper with 100 µM phenolphthalein, (2) corresponds with filter paper modified with 0.1 mol/L beta-cyclodextrin with a cholesterol concentration of 125 µM, (3) corresponds with filter paper modified with 0.1 mol/L beta-cyclodextrin with a cholesterol concentration of 63 µM, (4) corresponds with filter paper modified with 0.1 mol/L beta-cyclodextrin with a cholesterol concentration of 38 µM, (5) corresponds with filter paper modified with 0.1 mol/L beta-cyclodextrin with a cholesterol concentration of 6 µM, (6) corresponds with filter paper modified with 0.1 mol/L beta-cyclodextrin with a cholesterol concentration of 3 µM, (7) corresponds with filter paper modified with 0.1 mol/L beta-cyclodextrin with a cholesterol concentration of 1.5 µM, (8) corresponds with filter paper modified with 0.1 mol/L beta-cyclodextrin with a cholesterol concentration of 0.75 µM, (9) corresponds with filter paper modified with 0.1 mol/L beta-cyclodextrin with a cholesterol concentration of 0.15 µM, and (10) corresponds with filter paper that is modified with 0.1 mol/L beta-cyclodextrin and 100 µM phenolphthalein.

Due to the experimental error (5%) associated to the detection, percent recovery of 15% was considered as a limit of detection to be safe in the screening. The response was linearly proportional to cholesterol concentration from 0.15 µM to 125 µM, with a detection limit of 0.08 µM. The naked color changes were also obvious to monitor the level of cholesterol. These results successfully demonstrated the applicability of the proposed methodology for both qualitative and quantitative monitoring of cholesterol levels.

The method specificity and selectivity for cholesterol was also checked by investigating the developed method for possible interfering compounds including glucose, ascorbic acid and uric acid.

Figure 7A:
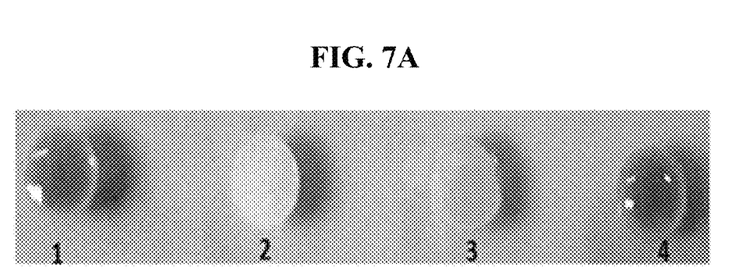
FIG. 7A is an image showing whether phenolphthalein exhibits absorbance recovery in the presence of ascorbic acid.
Figure 7B:
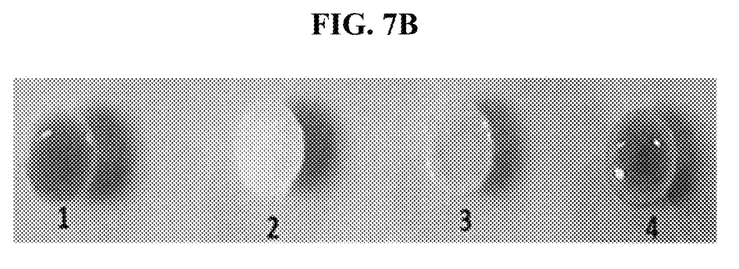
FIG. 7B is an image showing whether phenolphthalein exhibits absorbance recovery in the presence of glucose.
Figure 7C:
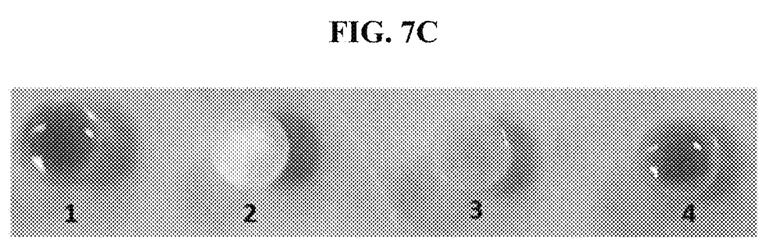
FIG. 7C is an image showing whether phenolphthalein exhibits absorbance recovery in the presence of uric acid.

FIG. 7A is an image showing whether phenolphthalein exhibits absorbance recovery in the presence of ascorbic acid. FIG. 7B is an image showing whether phenolphthalein exhibits absorbance recovery in the presence of glucose. FIG. 7C is an image showing whether phenolphthalein exhibits absorbance recovery in the presence of uric acid.

In FIGS. 7A, 7B, and 7C, (1) corresponds with unmodified filter paper with 100 µM Phenolphthalein, (2) corresponds with filter paper modified with 0.1 mol/L beta-cyclodextrin as well as 100 µM phenolphthalein, (3) corresponds with filter paper modified with 0.1 mol/L beta-cyclodextrin as well as 100 µM phenolphthalein and 40 µM interfering molecule (i.e., ascorbic acid for FIG. 7A, glucose for FIG. 7B, and uric acid for FIG. 7C), and (4) modified with 0.1 mol/L beta-cyclodextrin as well as 100 µM phenolphthalein and 40 µM cholesterol.

As shown in FIGS. 7A, 7B, and 7C, the common interfering compounds (i.e., ascorbic acid for FIG. 7A, glucose for FIG. 7B, and uric acid for FIG. 7C) have no evident absorbance recovery even at much higher concentrations than cholesterol. It can be concluded from these results that the proposed colorimetric method has good selectivity for determination of cholesterol. The slight variation in the color appearance may be attributed to the physical hindrance of the interfering molecules, preventing the host-guest interaction of beta-cyclodextrin with phenolphthalein to a negligible extent. The lower concentrations of interfering molecules did not show any response of color recovery.

In order to demonstrate the applicability of the designed method, the developed approach was used to detect cholesterol in the human serum sample. The obtained results with recovery values are included in the Table 1. The average recovery values for cholesterol concentrations were from 100.15% to 108.34%. Similarly, the precision of the method was also presented in the Table 1. The relative standard deviation values were obtained for each concentration level. Good recovery values and good precision values for cholesterol detection based on proposed assay reveals that the filter paper based colorimetric approach was useful to reduce the matrix effect of human serum sample. It is obvious that the proposed method may find spread applications in clinical analysis of cholesterol in various types of real samples such as human serum, food products, etc.

TABLE 1

Recovery percentages obtained in human serum samples

| Spiked Cholesterol (μM) | [Cholesterol]$^b$ (μM) | R.S.D % | R.E % | R$^a$ % |
|---|---|---|---|---|
| 125 | 125.19 | 5 | 0.15 | 100.15 |
| 63 | 64.17 | 5 | 0.85 | 101.85 |
| 6 | 6.5 | 5 | 8.34 | 108.34 |

[Cholesterol]$^b$ = found Cholesterol concentration,
R.S.D % = relative standard deviation percentage;
R.E % = relative error percentage;
R$^a$ % = recovery percentage.

Materials and Methods

Materials and Reagents

Phenolphthalein, β-Cyclodextrin, dimethyl sulfoxide (DMSO), methanol, sodium hydroxide (NaOH), acetone (99%), glucose, uric acid, ascorbic acid, and PBS tablets were purchased from Sigma-Aldrich (Taufkirchen, Germany). Cholesterol powder was obtained from Merck. Epichlorohydrin was received from BDH (UK). Qualitative filter paper with 12.5 mm diameter was used in experiments obtained from Whatman (UK). Deionized water from ELGA PURELAB® Ultra water deionizer (High Wycombe, UK) was used to make solutions.

Apparatus

The absorbance of sample solutions was detected by UV-Vis Spectrophotometer (lambda Perkin Elmer). Sonication of samples was performed on WiseClean WUC Digital Ultrasonicator (Germany)

UV/Vis Spectrophotometric Analysis

Optimization of Beta-Cyclodextrin Concentration

In order to optimize the beta-cyclodextrin concentration, quenching in the color intensity of 35 μM Phenolphthalein solution was monitored by UV/Vis spectrophotometer under varying concentration of beta-cyclodextrin (0.1, 0.25, 0.5, 0.75, 1 mg/ml). Phosphate buffer solution (PBS) was used to make a final volume of 2 ml for each assays.

Cholesterol Complexation Study

To have an insight the complexation phenomena, varying concentrations of cholesterol (5, 50, 100, 150, 200 μM) were added to an optimal concentration of beta-cyclodextrin (0.75 mg/mL). The final volume of the assays were made 2 mL with the addition of PBS prior to perform the analysis.

Quantitative Analysis of Cholesterol

For quantitative measurement of cholesterol, the optimized concentrations of beta-cyclodextrin (0.75 mg/mL) and phenolphthalein (35 μM) were used. The phenolphthalein (35 μM) as a single component in the buffer media was characterized with a good UV/Visible response, while incubation of beta-cyclodextrin (0.75 mg/mL) quenched the response of phenolphthalein. The addition of varying concentrations of cholesterol (5-500 μM) along with beta-cyclodextrin (0.75 mg/mL) recovered the absorption characteristic of phenolphthalein in linear proportion to the concentrations. To perform all the assays, final volume was made 2 mL with the addition of PBS buffer.

Filter Paper Based Assay for Cholesterol Analysis

Preparation of Beta-Cyclodextrin Modified Filter Paper

Whatman filter papers were cut into appropriate size and put into 5 mol L$^{-1}$ sodium hydroxide solution for 30 min. Afterwards, the filter paper was incubated into mixture solution of sodium hydroxide (5 mol L$^{-1}$), dimethylsulfoxide, and epichlorohydrin of 2:4:5 (V/V/V), and sonicated in the ultrasonic bath for 1 hour at 45° C. Subsequently, filter papers were rinsed with pure water and an optimized concentration of beta-cyclodextrin in the presence of 5 mol L$^{-1}$ sodium hydroxide solution was used to modify the filter paper surface. The sonication process was performed for a time period of 1 h at 45° C. Afterwards, the modified filter papers were washed with pure water, until the pH value of 7 was achieved. Finally, after incubation in the acetone media, modified filter papers were dried at ambient temperature. The as prepared filter papers were put in the desiccator for subsequent use to perform the quantitative analysis of cholesterol Analysis of Cholesterol on Modified Filter Paper beta-cyclodextrin modified filter were colorless. The incubation of 100 μM phenolphthalein on unmodified filter retained its optical characteristics. However, the color of 100 μM phenolphthalein was completely quenched on beta-cyclodextrin modified filter papers (0.1 mol/L) instantaneously. The presence of varying concentrations of cholesterol (0.15-125 μM) on the filter paper reduced the quenching properties of beta-cyclodextrin, and resulted in the recovery of optical properties of 100 μM phenolphthalein. The change in the color/optical properties of filter was monitored through scanning of the filter papers or by taking a photograph with a smart phone, and further date treatment of data was performed in Adobe® Photoshop® to get the RGB (Red, Green, and Blue) value for individual paper. The recovered optical response was directly proportional to the concentrations of incubated cholesterol, and was used to draw a calibration curve.

Interference Study

The specificity of the developed paper based sensor was evaluated by performing control experiments using nonspecific binding molecules including glucose, ascorbic acid, and uric acid. Experiments were performed under similar conditions as those described for the detection of cholesterol on beta-cyclodextrin modified filter papers (0.1 mol/L) in the presence of 100 μM phenolphthalein. The response of 40 μM of ascorbic acid, glucose, and uric acid was monitored and the optical results were compared with those of obtained under similar concentration of cholesterol.

Human Serum Sample Analysis

The practical applicability of paper based sensor was demonstrated by analyzing the cholesterol level in human serum sample. Absolute human serum sample was spiked with different concentrations of cholesterol (125, 100, and 63 μM) and the analysis were performed under similar conditions as those described for cholesterol analysis in buffer sample in the presence of 100 μM phenolphthalein on beta-cyclodextrin modified filter papers (0.1 mol/L). Based on the optical output signal, the percentage recovery response was calculated for each concentration from the standard calibration curve.

Data Analysis

Filter based sensors were scanned in color photo Scanner or the images were taken with a smart phone devise, and saved as JPEG images. These images were further imported into Adobe Photoshop and subsequently examined with the eyedropper tool. The images were decomposed into its red, green and blue component (RGB components. Analysis using the green (G) color channel permitted for detection of lowest concentrations of cholesterol with greatest sensitivity and linearity of all color analysis options and thus all calibrations were created using green color intensity.

Method Advantages

The method offers selectivity through selective host-guest interaction. The method does not use any specific biomolecules such enzyme/antibody. Filter paper was used as a cheap transduction platform to generate the optical signal.

The generated output optical signals does not require any specific instrument to get the interpretable data. Only a smart phone is needed to complete the assay. Modified filter paper was stable over an extend period of time, which makes assay ready to use and highly suitable for decentralized clinical assay. The proposed assay is highly cost effective and does not required any skilled person to operate. The method design requires a minimum volume (10 µL) of the sample to be analyzed. The assay response is very quick and complete analysis can be completed within time period of 1 min, as compared to the long analysis time of the literature reported or commonly practiced methodologies for cholesterol monitoring.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A method for colorimetric detection of cholesterol in a sample, the method comprising:
   adding beta-cyclodextrin and cholesterol to a phenolphthalein indicator solution with a phosphate buffer solution to create a solution medium; and
   quantifying the cholesterol as a function of a complexed beta-cyclodextrin in the solution medium.

2. The method of claim 1, further comprising,
   comparing an efficiency of the beta-cyclodextrin to a quenched phenolphthalein in the phosphate buffer solution at different pHs.

3. The method of claim 1, wherein a change in a pH of the phosphate buffer solution is associated with a color intensity of the phenolphthalein.

4. The method of claim 1, further comprising:
   comparing the beta-cyclodextrin complexation with the cholesterol at different pHs in the phosphate buffer solution.

5. The method of claim 1, further comprising:
   recording a cholesterol complexation with the beta-cyclodextrin under varying concentrations of the cholesterol.

6. The method of claim 1, further comprising:
   detecting different concentrations of the cholesterol by monitoring recovery of a phenolphthalein color using an ultraviolet/visible spectrophotometer; and
   determining an amount of total cholesterol present in a sample based on the detection,
   wherein the recovery of phenolphthalein color is based on competitive binding between the cholesterol and phenolphthalein for the beta-cyclodextrin.

7. A method for colorimetric detection of cholesterol in a human serum sample using a filter paper based transducer platform, the method comprising the steps of:
   providing sonication time and concentration of a beta-cyclodextrin for the modification of a filter paper with the beta-cyclodextrin;
   quantifying the cholesterol based on recovery of a beta-cyclodextrin quenched phenolphthalein color on the filter paper based transducer platform;
   checking a response of cholesterol interfering compounds for a filter paper based assay; and
   detecting the cholesterol in the human serum sample.

8. The method of claim 7, wherein color recovery of phenolphthalein in the presence of cholesterol is achieved on beta-cyclodextrin modified filter paper transducers subject to different sonication time intervals during modification, indicating sonication time dependency on color recovery.

9. The method of claim 7, wherein the filter paper is modified with a range of different concentrations of the beta-cyclodextrin.

10. The method of claim 7, wherein a quantitative analysis for monitoring cholesterol is performed and a linear response in the form of increasing phenolphthalein color recovery results with an increase in cholesterol concentration.

11. The method of claim 10, further comprising the step of:
    comparing the phenolphthalein color recovery for a given cholesterol concentration at different time intervals.

12. The method of claim 7, wherein the specificity and selectivity of developed paper based sensor for the cholesterol is established in the presence of an interfering compound, and wherein the interfering compound is selected from the group consisting of glucose, ascorbic acid, and uric acid.

13. The method of claim 7, wherein the stability of a filter paper based sensor is evaluated for extended intervals of time.

14. A system for the colorimetric determination of cholesterol in a sample, the system comprising:
    a sample;
    a beta-cyclodextrin modified filter paper;
    a phenolphthalein indicator solution in phosphate buffer solution;
    a smart phone; and
    software to process images.

15. The system of claim 14, wherein:
    the images are taken with the smart phone or are scanned with a color photo scanner, and
    the images are saved as Joint Photographic Expert Group (JPEG) images.

16. The system of claim 15, wherein the saved JPEG images are imported into image processing software and examined with different software tools.

17. The system of claim 15, wherein the saved JPEG images are disintegrated into red, green, and blue (RGB) components.

18. The system of claim 15, wherein the detection of a lowest concentration of the cholesterol is achieved with greatest sensitivity by a permitting green (G) color channel for analysis.

19. A method, comprising:
    adding a phenolphthalein indicator solution in a phosphate buffer solution to a modified filter paper containing beta-cyclodextrin;
    adding a sample containing cholesterol to the modified filter paper to create a finalized filter paper;
    taking an image of the finalized filter paper; and
    determining a total amount of cholesterol in the sample by comparing the image of the finalized filter paper to control images.

* * * * *

UNITED STATES PATENT AND TRADEMARK OFFICE
CERTIFICATE OF CORRECTION

| | | |
|---|---|---|
| PATENT NO. | : 10,684,277 B2 | Page 1 of 1 |
| APPLICATION NO. | : 15/991572 | |
| DATED | : June 16, 2020 | |
| INVENTOR(S) | : Akhtar Hayat and Muhammad Azhar Hayat Nawaz | |

It is certified that error appears in the above-identified patent and that said Letters Patent is hereby corrected as shown below:

On the Title Page

Item (73) Assignee: update assignee as:
"COMSATS University Islamabad, Islamabad (PK)"

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*